US010471017B2

(12) United States Patent
Lai et al.

(10) Patent No.: US 10,471,017 B2
(45) Date of Patent: *Nov. 12, 2019

(54) TASTE-MASKED PHARMACEUTICAL COMPOSITIONS WITH GASTROSOLUBLE PORE-FORMERS

(71) Applicant: Adare Pharmaceuticals, Inc., Lawrenceville, NJ (US)

(72) Inventors: Jin-Wang Lai, Springboro, OH (US); Gopi M. Venkatesh, Vandalia, OH (US); Ken Kangyi Qian, Manchester, CT (US)

(73) Assignee: ADARE PHARMACEUTICALS, INC., Lawrenceville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/387,317

(22) Filed: Dec. 21, 2016

(65) Prior Publication Data

US 2017/0105942 A1    Apr. 20, 2017

Related U.S. Application Data (63) Continuation of application No. 11/256,653, filed on Oct. 21, 2005, now abandoned.
(Continued)

(51) Int. Cl.
*A61K 9/50* (2006.01)
*A61K 31/4045* (2006.01)
(Continued)

(52) U.S. Cl.
CPC .......... *A61K 9/5078* (2013.01); *A61K 9/0056* (2013.01); *A61K 9/2081* (2013.01);
(Continued)

(58) Field of Classification Search
CPC .. A61K 9/0056; A61K 9/2077; A61K 9/2081; A61K 9/501; A61K 9/5078; A61K 9/5047
(Continued)

(56) References Cited

U.S. PATENT DOCUMENTS 3,184,386 A    5/1965  Stephenson
3,558,768 A    1/1971  Klippel
(Continued)

FOREIGN PATENT DOCUMENTS

EP    0052492 B1    2/1984
EP    0166440 A2    1/1986
(Continued)

OTHER PUBLICATIONS

"European Search Report," 6 pages, EP appl. No. 13167223.0 (dated Aug. 21, 2013).
(Continued)

*Primary Examiner* — Rachael E Bredefeld
(74) *Attorney, Agent, or Firm* — Cooley LLP (57) ABSTRACT

There is provided a method for preparing an orally disintegrating tablet (ODT) composition comprising microparticles of one or more task-masked active pharmaceutical ingredient(s), rapidly-dispersing microgranules, and other optional, pharmaceutically acceptable excipients wherein the ODT disintegrates on contact with saliva in the buccal cavity forming a smooth, easy-to-swallow suspension. Furthermore, the microparticles (crystals, granules, beads or pellets containing the active), coated with a taste-masking membrane comprising a water-insoluble polymer and one or more gastrosoluble inorganic or organic pore-formers (practically insoluble in water and saliva, but soluble in an acidic buffer), exhibit acceptable taste-masking when placed in the oral cavity and provide rapid, substantially-complete release of the dose on entry into the stomach.

26 Claims, 5 Drawing Sheets

Related U.S. Application Data (60) Provisional application No. 60/621,144, filed on Oct. 21, 2004.

(51) Int. Cl.
  *A61K 31/495* (2006.01)
  *A61K 31/135* (2006.01)
  *A61K 9/00* (2006.01)
  *A61K 9/20* (2006.01)

(52) U.S. Cl.
  CPC ............ *A61K 9/501* (2013.01); *A61K 9/5026* (2013.01); *A61K 9/5047* (2013.01); *A61K 31/135* (2013.01); *A61K 31/4045* (2013.01); *A61K 31/495* (2013.01)

(58) Field of Classification Search
  USPC ........................................................ 424/470
  See application file for complete search history.

(56) References Cited

U.S. PATENT DOCUMENTS

| | | |
|---|---|---|
| 3,885,026 A | 5/1975 | Heinemann et al. |
| 4,078,051 A | 3/1978 | Pomot et al. |
| 4,138,475 A | 2/1979 | McAinsh et al. |
| 4,248,857 A | 2/1981 | DeNeale et al. |
| 4,292,017 A | 9/1981 | Doepel |
| 4,305,502 A | 12/1981 | Gregory et al. |
| 4,369,172 A | 1/1983 | Schor et al. |
| 4,371,516 A | 2/1983 | Gregory et al. |
| 4,389,330 A | 6/1983 | Tice et al. |
| 4,389,393 A | 6/1983 | Schor et al. |
| 4,542,042 A | 9/1985 | Samejima et al. |
| 4,556,678 A | 12/1985 | Hsiao |
| 4,587,118 A | 5/1986 | Hsiao |
| 4,628,098 A | 12/1986 | Nohara et al. |
| 4,661,647 A | 4/1987 | Serpelloni et al. |
| 4,670,459 A | 6/1987 | Sjoerdsma |
| 4,689,333 A | 8/1987 | Nohara et al. |
| 4,698,101 A | 10/1987 | Koivurinta |
| 4,708,867 A | 11/1987 | Hsiao |
| 4,713,248 A | 12/1987 | Kjornaes et al. |
| 4,716,041 A | 12/1987 | Kjornaes et al. |
| 4,728,512 A | 3/1988 | Mehta et al. |
| 4,743,248 A | 5/1988 | Bartoo et al. |
| 4,752,470 A | 6/1988 | Mehta |
| 4,757,090 A | 7/1988 | Salpekar et al. |
| 4,760,093 A | 7/1988 | Blank et al. |
| 4,780,318 A | 10/1988 | Appelgren et al. |
| 4,786,508 A | 11/1988 | Ghebre-Sellassie et al. |
| 4,800,087 A | 1/1989 | Mehta |
| 4,803,213 A | 2/1989 | Iida et al. |
| 4,824,675 A | 4/1989 | Wong et al. |
| 4,832,880 A | 5/1989 | Staniforth |
| 4,840,799 A | 6/1989 | Appelgren et al. |
| 4,851,226 A | 7/1989 | Julian et al. |
| 4,851,229 A | 7/1989 | Magruder et al. |
| 4,863,742 A | 9/1989 | Panoz et al. |
| 4,871,549 A | 10/1989 | Ueda et al. |
| 4,874,613 A | 10/1989 | Hsiao |
| 4,886,669 A | 12/1989 | Ventouras |
| 4,892,741 A | 1/1990 | Ohm et al. |
| 4,894,240 A | 1/1990 | Geoghegan et al. |
| 4,898,737 A | 2/1990 | Panoz et al. |
| 4,915,949 A | 4/1990 | Wong et al. |
| 4,938,968 A | 7/1990 | Mehta |
| 4,946,684 A | 8/1990 | Blank et al. |
| 4,957,745 A | 9/1990 | Jonsson et al. |
| 4,968,508 A | 11/1990 | Oren et al. |
| 4,971,805 A | 11/1990 | Kitanishi et al. |
| 4,983,401 A | 1/1991 | Eichel et al. |
| 5,006,345 A | 4/1991 | Lang |
| 5,011,692 A | 4/1991 | Fujioka et al. |
| 5,013,557 A | 5/1991 | Tai |
| 5,013,743 A | 5/1991 | Iwahi et al. |
| 5,017,122 A | 5/1991 | Staniforth |
| 5,017,381 A | 5/1991 | Maruyama et al. |
| 5,026,559 A | 6/1991 | Eichel et al. |
| 5,026,560 A | 6/1991 | Makino et al. |
| 5,039,540 A | 8/1991 | Ecanow |
| 5,045,321 A | 9/1991 | Makino et al. |
| 5,073,374 A | 12/1991 | McCarty |
| 5,075,114 A | 12/1991 | Roche |
| 5,079,018 A | 1/1992 | Ecanow |
| 5,082,669 A | 1/1992 | Shirai et al. |
| 5,084,278 A | 1/1992 | Mehta |
| 5,093,132 A | 3/1992 | Makino et al. |
| 5,104,648 A | 4/1992 | Denton et al. |
| 5,112,616 A | 5/1992 | McCarty |
| 5,133,974 A | 7/1992 | Paradissis et al. |
| 5,137,733 A | 8/1992 | Noda et al. |
| 5,149,542 A | 9/1992 | Valducci |
| 5,160,680 A | 11/1992 | Serpelloni et al. |
| 5,169,640 A | 12/1992 | France et al. |
| 5,178,878 A | 1/1993 | Wehling et al. |
| 5,204,121 A | 4/1993 | Bucheler et al. |
| 5,211,957 A | 5/1993 | Hagemann et al. |
| 5,213,808 A | 5/1993 | Bar-Shalom et al. |
| 5,229,131 A | 7/1993 | Amidon et al. |
| 5,229,135 A | 7/1993 | Philippon et al. |
| 5,238,686 A | 8/1993 | Eichel et al. |
| 5,252,337 A | 10/1993 | Powell |
| 5,256,699 A | 10/1993 | Murphy et al. |
| 5,260,068 A | 11/1993 | Chen |
| 5,260,069 A | 11/1993 | Chen |
| 5,275,827 A | 1/1994 | Spinelli et al. |
| 5,376,384 A | 12/1994 | Eichel et al. |
| 5,403,893 A | 4/1995 | Tanaka et al. |
| 5,409,711 A | 4/1995 | Mapelli et al. |
| 5,433,959 A | 7/1995 | Makino et al. |
| 5,439,689 A | 8/1995 | Hendrickson et al. |
| 5,445,829 A | 8/1995 | Paradissis et al. |
| 5,464,632 A | 11/1995 | Cousin et al. |
| 5,466,464 A | 11/1995 | Masaki et al. |
| 5,470,584 A | 11/1995 | Hendrickson et al. |
| 5,472,708 A | 12/1995 | Chen |
| 5,478,573 A | 12/1995 | Eichel et al. |
| 5,489,436 A | 2/1996 | Hoy et al. |
| 5,501,861 A | 3/1996 | Makino et al. |
| 5,506,345 A | 4/1996 | Riley et al. |
| 5,508,040 A | 4/1996 | Chen |
| 5,529,790 A | 6/1996 | Eichel et al. |
| 5,536,507 A | 7/1996 | Abramowitz et al. |
| 5,567,441 A | 10/1996 | Chen |
| 5,576,014 A | 11/1996 | Mizumoto et al. |
| 5,609,883 A | 3/1997 | Valentine et al. |
| 5,612,059 A | 3/1997 | Cardinal et al. |
| 5,616,345 A | 4/1997 | Geoghegan et al. |
| 5,629,017 A | 5/1997 | Pozzi et al. |
| 5,639,475 A | 6/1997 | Bettman et al. |
| 5,643,630 A | 7/1997 | Hinzpeter et al. |
| 5,700,492 A | 12/1997 | Morimoto et al. |
| 5,720,974 A | 2/1998 | Makino et al. |
| 5,738,875 A | 4/1998 | Yarwood et al. |
| 5,747,068 A | 5/1998 | Mendizabal |
| 5,762,961 A | 6/1998 | Roser et al. |
| 5,788,987 A | 8/1998 | Busetti et al. |
| 5,807,577 A | 9/1998 | Ouali |
| 5,837,284 A | 11/1998 | Mehta et al. |
| 5,837,285 A | 11/1998 | Nakamichi et al. |
| 5,837,379 A | 11/1998 | Chen et al. |
| 5,840,329 A | 11/1998 | Bai |
| 5,876,759 A | 3/1999 | Gowan, Jr. |
| 5,891,474 A | 4/1999 | Busetti et al. |
| 5,900,252 A | 5/1999 | Calanchi et al. |
| 5,908,638 A | 6/1999 | Huber et al. |
| 5,968,554 A | 10/1999 | Beiman et al. |
| 6,024,981 A | 2/2000 | Khankari et al. |
| 6,024,982 A | 2/2000 | Oshlack et al. |
| 6,033,687 A | 3/2000 | Heinicke et al. |
| 6,039,979 A | 3/2000 | Gendrot et al. |
| 6,096,340 A | 8/2000 | Chen et al. |
| 6,099,859 A | 8/2000 | Cheng et al. |

(56) References Cited

U.S. PATENT DOCUMENTS

| | | |
|---|---|---|
| 6,099,863 A | 8/2000 | Gilis et al. |
| 6,099,865 A | 8/2000 | Augello et al. |
| 6,103,263 A | 8/2000 | Lee et al. |
| 6,106,861 A | 8/2000 | Chaveau et al. |
| 6,106,862 A | 8/2000 | Chen et al. |
| 6,123,962 A | 9/2000 | Makino et al. |
| 6,129,933 A | 10/2000 | Oshlack et al. |
| 6,136,345 A | 10/2000 | Grimmett et al. |
| 6,139,865 A | 10/2000 | Friend et al. |
| 6,139,877 A | 10/2000 | Debregeas et al. |
| 6,153,220 A | 11/2000 | Cumming et al. |
| 6,162,463 A | 12/2000 | Lippa |
| 6,169,105 B1 | 1/2001 | Wong et al. |
| 6,183,776 B1 | 2/2001 | Depui et al. |
| 6,190,692 B1 | 2/2001 | Busetti et al. |
| 6,221,392 B1 | 4/2001 | Khankari et al. |
| 6,221,402 B1 | 4/2001 | Itoh et al. |
| 6,228,398 B1 | 5/2001 | Devane et al. |
| 6,269,615 B1 | 8/2001 | Amborn et al. |
| 6,287,599 B1 | 9/2001 | Burnside et al. |
| 6,316,029 B1 | 11/2001 | Jain et al. |
| 6,328,994 B1 | 12/2001 | Shimizu et al. |
| 6,344,215 B1 | 2/2002 | Bettman et al. |
| 6,350,470 B1 | 2/2002 | Pather et al. |
| 6,350,471 B1 | 2/2002 | Seth |
| 6,365,182 B1 | 4/2002 | Khankari et al. |
| 6,368,625 B1 | 4/2002 | Siebert et al. |
| 6,368,628 B1 | 4/2002 | Seth |
| 6,372,253 B1 | 4/2002 | Daggy et al. |
| 6,391,335 B1 | 5/2002 | Pather et al. |
| 6,413,549 B2 | 7/2002 | Green et al. |
| 6,420,473 B1 | 7/2002 | Chittamuru et al. |
| 6,432,534 B1 | 8/2002 | Hayakawa et al. |
| 6,465,009 B1 | 10/2002 | Liu et al. |
| 6,465,010 B1 | 10/2002 | Lagoviyer et al. |
| 6,495,160 B2 | 12/2002 | Esposito et al. |
| 6,500,454 B1 | 12/2002 | Percel et al. |
| 6,500,457 B1 | 12/2002 | Midha et al. |
| 6,500,894 B1 | 12/2002 | Lenti et al. |
| 6,509,036 B2 | 1/2003 | Pather et al. |
| 6,531,152 B1 | 3/2003 | Lerner et al. |
| 6,551,617 B1 | 4/2003 | Corbo et al. |
| 6,579,535 B2 | 6/2003 | Valentine et al. |
| 6,596,311 B1 | 7/2003 | Dobetti |
| 6,602,521 B1 | 8/2003 | Ting et al. |
| 6,627,223 B2 | 9/2003 | Percel et al. |
| 6,641,838 B2 | 11/2003 | Pather et al. |
| 6,660,382 B2 | 12/2003 | Nouri et al. |
| 6,663,888 B2 | 12/2003 | Percel et al. |
| 6,663,893 B2 | 12/2003 | Corbo et al. |
| 6,740,341 B1 | 5/2004 | Holt et al. |
| 6,897,205 B2 | 5/2005 | Beckert et al. |
| 7,048,945 B2 | 5/2006 | Percel et al. |
| 8,071,128 B2 | 12/2011 | Ohta et al. |
| 8,357,396 B2 | 1/2013 | Ohta et al. |
| 8,367,111 B2 | 2/2013 | Venkatesh et al. |
| 8,545,881 B2 | 10/2013 | Venkatesh et al. |
| 8,747,895 B2 | 6/2014 | Venkatesh et al. |
| 8,945,618 B2 | 2/2015 | Ohta et al. |
| 8,956,650 B2 | 2/2015 | Ohta et al. |
| 9,040,086 B2 | 5/2015 | Percel et al. |
| 9,161,918 B2 | 10/2015 | Venkatesh et al. |
| 9,161,919 B2 | 10/2015 | Venkatesh et al. |
| 9,358,214 B2 | 6/2016 | Percel et al. |
| 9,566,249 B2 | 2/2017 | Venkatesh et al. |
| 9,579,293 B2 | 2/2017 | Venkatesh et al. |
| 9,884,014 B2 | 2/2018 | Venkatesh et al. |
| 2001/0007680 A1 | 7/2001 | Kolter et al. |
| 2001/0014340 A1 | 8/2001 | Ohta et al. |
| 2001/0046964 A1 | 11/2001 | Percel et al. |
| 2002/0054907 A1 | 5/2002 | Devane et al. |
| 2002/0077348 A1 | 6/2002 | Dean et al. |
| 2002/0142034 A1 | 10/2002 | Shimizu et al. |
| 2002/0187190 A1 | 12/2002 | Cade et al. |
| 2003/0064108 A1 | 4/2003 | Lukas et al. |
| 2003/0096791 A1 | 5/2003 | Gupte et al. |
| 2003/0113374 A1 | 6/2003 | Percel et al. |
| 2003/0134884 A1 | 7/2003 | Hazama et al. |
| 2003/0157173 A1 | 8/2003 | Percel et al. |
| 2003/0161888 A1 | 8/2003 | Fernandez et al. |
| 2003/0215500 A1 | 11/2003 | Ohta et al. |
| 2004/0047906 A1 | 3/2004 | Percel et al. |
| 2004/0121010 A1 | 6/2004 | Hirsh et al. |
| 2004/0122106 A1 | 6/2004 | Ohta et al. |
| 2004/0126427 A1 | 7/2004 | Venkatesh et al. |
| 2004/0131682 A1 | 7/2004 | Percel et al. |
| 2004/0137156 A1 | 7/2004 | Lee et al. |
| 2004/0242536 A1 | 12/2004 | Khoo et al. |
| 2005/0025824 A1 | 2/2005 | Percel et al. |
| 2005/0118268 A1 | 6/2005 | Percel et al. |
| 2005/0152974 A1 | 7/2005 | Boehm et al. |
| 2005/0232988 A1 | 10/2005 | Venkatesh et al. |
| 2005/0269722 A1 | 12/2005 | De Luigi Bruschi et al. |
| 2006/0057199 A1 | 3/2006 | Venkatesh et al. |
| 2006/0078614 A1 | 4/2006 | Venkatesh et al. |
| 2006/0105038 A1 | 5/2006 | Lai et al. |
| 2006/0105039 A1 | 5/2006 | Lai et al. |
| 2006/0121112 A1 | 6/2006 | Jenkins et al. |
| 2006/0233892 A1 | 10/2006 | Hendrix |
| 2006/0246134 A1 | 11/2006 | Venkatesh |
| 2006/0269607 A1 | 11/2006 | Percel et al. |
| 2007/0264358 A1 | 11/2007 | Wittlin |
| 2008/0069878 A1 | 3/2008 | Venkatesh et al. |
| 2009/0149433 A1 | 6/2009 | Phillips |
| 2009/0263480 A1 | 10/2009 | Lai et al. |
| 2011/0212171 A1 | 9/2011 | Venkatesh et al. |
| 2012/0128771 A1 | 5/2012 | Venkatesh |
| 2012/0135076 A1 | 5/2012 | Ohta et al. |
| 2013/0281546 A1 | 10/2013 | Morimoto |
| 2014/0193496 A1 | 7/2014 | Ohta et al. |
| 2016/0038431 A1 | 2/2016 | Venkatesh et al. |
| 2016/0106683 A1 | 4/2016 | Venkatesh et al. |
| 2017/0112774 A1 | 4/2017 | Venkatesh et al. |

FOREIGN PATENT DOCUMENTS

| | | |
|---|---|---|
| EP | 0239361 A1 | 9/1987 |
| EP | 0349103 A1 | 1/1990 |
| EP | 0357369 A2 | 3/1990 |
| EP | 0391518 A2 | 10/1990 |
| EP | 0431877 A1 | 6/1991 |
| EP | 0453001 A1 | 10/1991 |
| EP | 0516345 A1 | 12/1992 |
| EP | 0538034 A1 | 4/1993 |
| EP | 0553777 A2 | 8/1993 |
| EP | 0650826 A1 | 5/1995 |
| EP | 0721777 A2 | 7/1996 |
| EP | 0815931 A1 | 1/1998 |
| EP | 0293347 A1 | 11/1998 |
| EP | 0294493 A1 | 12/1998 |
| EP | 0914818 A1 | 5/1999 |
| EP | 0914823 A1 | 5/1999 |
| EP | 1010423 A2 | 6/2000 |
| EP | 0582396 B1 | 1/2001 |
| EP | 1070497 A1 | 1/2001 |
| EP | 1072257 A1 | 1/2001 |
| EP | 1157690 A1 | 11/2001 |
| EP | 1156786 B1 | 3/2003 |
| EP | 1366759 A1 | 12/2003 |
| EP | 0914823 B1 | 12/2004 |
| EP | 2319498 A1 | 5/2011 |
| FR | 2679451 A1 | 1/1993 |
| FR | 2766089 A1 | 1/1999 |
| FR | 2778848 A1 | 11/1999 |
| GB | 2053787 A | 2/1981 |
| GB | 8824392.8 | 9/1989 |
| GB | 2224207 A | 5/1990 |
| JP | 41-11273 B | 6/1966 |
| JP | 49-69819 | 7/1974 |
| JP | 55-129224 A | 10/1980 |
| JP | 56-014098 A | 10/1981 |
| JP | 61-143316 A | 7/1986 |
| JP | 62-61916 A | 3/1987 |
| JP | 62-50445 B2 | 10/1987 |

(56) References Cited

FOREIGN PATENT DOCUMENTS

| | | |
|---|---|---|
| JP | 62-242616 A | 10/1987 |
| JP | 62-246513 A | 10/1987 |
| JP | 62-252723 A | 11/1987 |
| JP | 63-162619 A | 7/1988 |
| JP | 63-270624 A | 11/1988 |
| JP | 1-503385 A | 11/1989 |
| JP | 1-313420 A | 12/1989 |
| JP | 2-500747 A | 3/1990 |
| JP | 2-164824 A | 6/1990 |
| JP | 2-172918 A | 7/1990 |
| JP | 2-289512 A | 11/1990 |
| JP | 3-240724 A | 10/1991 |
| JP | 4-224517 A | 8/1992 |
| JP | 5-271054 A | 10/1993 |
| JP | 5-310558 A | 11/1993 |
| JP | 6-116140 A | 4/1994 |
| JP | 6-53658 B2 | 7/1994 |
| JP | 6-321790 A | 11/1994 |
| JP | 7-69889 A | 3/1995 |
| JP | 7-124231 A | 5/1995 |
| JP | 8-503482 A | 4/1996 |
| JP | 8-175978 A | 7/1996 |
| JP | 2002-154948 A | 5/2002 |
| JP | 2003-522141 A | 7/2003 |
| JP | 2005-508922 A | 4/2005 |
| JP | 4991072 B2 | 8/2012 |
| NZ | 550608 A | 11/2005 |
| NZ | 554346 A | 5/2006 |
| WO | WO 88/08703 A1 | 11/1988 |
| WO | WO 88/08704 A2 | 11/1988 |
| WO | WO 92/10173 A1 | 6/1992 |
| WO | WO 93/00097 A1 | 1/1993 |
| WO | WO 93/12769 A1 | 7/1993 |
| WO | WO 93/13758 A1 | 7/1993 |
| WO | WO 93/15724 A1 | 8/1993 |
| WO | WO 94/08576 A1 | 4/1994 |
| WO | WO 94/12180 A1 | 6/1994 |
| WO | WO 97/41878 A1 | 11/1997 |
| WO | WO 97/47287 A1 | 12/1997 |
| WO | WO 99/04763 A1 | 2/1999 |
| WO | WO 99/59557 A1 | 11/1999 |
| WO | WO 00/25752 A1 | 5/2000 |
| WO | WO 00/33821 A1 | 6/2000 |
| WO | WO 00/42998 A1 | 7/2000 |
| WO | WO 00/51568 A1 | 9/2000 |
| WO | WO 00/59486 A2 | 10/2000 |
| WO | WO 01/13898 A2 | 3/2001 |
| WO | WO 01/72285 A1 | 10/2001 |
| WO | WO 01/80829 A2 | 11/2001 |
| WO | WO 02/13794 A1 | 2/2002 |
| WO | WO 02/43704 A1 | 6/2002 |
| WO | WO 02/057475 A1 | 7/2002 |
| WO | WO 02/085336 A1 | 10/2002 |
| WO | WO 03/013492 A1 | 2/2003 |
| WO | WO 03/039520 A1 | 3/2003 |
| WO | WO 03/026613 A1 | 4/2003 |
| WO | WO 03/041683 A2 | 5/2003 |
| WO | WO 03/043661 A1 | 5/2003 |
| WO | WO 03/047552 A2 | 6/2003 |
| WO | WO 2004/009058 A1 | 1/2004 |
| WO | WO 2004/022037 A1 | 3/2004 |
| WO | WO 2004/087111 A1 | 10/2004 |
| WO | WO 2005/097064 A2 | 10/2005 |
| WO | WO 2005/105049 A2 | 11/2005 |
| WO | WO 2006/047493 A2 | 5/2006 |

OTHER PUBLICATIONS

"Low Substituted Hydroxypropylcellulose," Official Monographs for Part II, 2001, NRF, JP XIV, pp. 942-943.

Ahmed, "Interview Summary," 2 pages, from U.S. Appl. No. 10/356,641 (dated Jul. 29, 2008).

Ahmed, "Interview Summary," 2 pages, from U.S. Appl. No. 10/356,641 (dated May 15, 2009).

Ahmed, "Interview Summary," 3 pages, from U.S. Appl. No. 10/356,641 (dated Sep. 8, 2006).

Ahmed, "Interview Summary," 4 pages, from U.S. Appl. No. 10/356,641 (dated Aug. 2, 2006).

Ahmed, "Office Action Summary," 10 pages, from U.S. Appl. No. 10/356,641 (dated Jan. 10, 2006).

Ahmed, "Office Action Summary," 13 pages, from U.S. Appl. No. 10/356,641 (dated Apr. 14, 2008).

Ahmed, "Office Action Summary," 15 pages, from U.S. Appl. No. 10/356,641 (dated Jun. 15, 2007).

Ahmed, "Office Action Summary," 20 pages, from U.S. Appl. No. 10/356,641 (dated Aug. 19, 2009).

Ahmed, "Office Action Summary," 24 pages, from U.S. Appl. No. 10/356,641 (dated Jun. 10, 2010).

Ahmed, "Office Action Summary," 44 pages, from U.S. Appl. No. 10/356,641 (dated Dec. 11, 2008).

Ahmed, "Office Action Summary," 7 pages, from U.S. Appl. No. 10/356,641 (dated Jun. 13, 2006).

Ahmed, "Office Action Summary," 7 pages, from U.S. Appl. No. 10/356,641 (dated Nov. 30, 2006).

Albrecht, "International Search Report," 6 pages, from International Patent Appl. No. PCT/US02/31535, European Patent Office (dated Feb. 3, 2003).

Anwar et al., "Chronotherapeutics for Cardiovascular Disease," Drugs 55(5):631-643 (1998).

Bauer et al., Pharmarzeutische Technologie, $5^{th}$ Edition, 1997, Govi Verlag Frankfurt, pp. 164-166 (translation attached).

Berigan, "Atomoxetine Used Adjunctively With Selective Serotonin Reuptake Inhibitors to Treat Depression," Prim. Care. Companion J. Clin. Psychiatry 6(2):93-94 (2004).

Bodmeier et al., "Theophylline Tablets Coated with Aqueous Latexes Containing Dispersed Pore Formers," J. Pharm. Sci. 79(10):925-928 (1990).

Chandra, "Examiner's first report on patent application 2005299490," 2 pages, Australia patent application No. 2005299490 (dated Mar. 12, 2010).

Citation in the Third Party Observation in the Opposition of European Patent No. EP 0914818 B1, dated Oct. 15, 1999, 9 pages.

Database WPI, Section Ch, Week 198748, Derwent Publications, Ltd., London, GB; Class A96; AN 1987-338131, XP002156870.

Duncan, "Examination Report," 2 pages, from New Zealand Patent Appl. No. 554346, New Zealand Patent Office, Wellington, New Zealand (dated May 20, 2009).

Experimental data provided by Opponent I the Opposition of European Patent No. Ep 0914818 B1, filed by Opponent on Jul. 23, 2009 (D36), 7 pages.

Fell, Letter to the Editor, J. Pharm. Pharmacol. 1968, vol. 20, pp. 657-658.

FMC Corporation Product Specification for Avicel PH, 2005.

Foreign non-patent publication from Japanese textbook, 1989, Hirokawa Publishing Co.(translation).

Foreign non-patent publication Sysmex No. FPBOSCJ001 (2007); (and English translation), 8 pages.

Fubara, "International Preliminary Examination Report," 3 pages, from International Patent Appl. No. PCT/US02/31535, European Patent Office (dated Jun. 19, 2003).

Gordon et al., "Effect of the Mode of Super Disintegrant Incorproration on Dissolution in Wet Granulated Tables," J. Pharm. Sci. 82:220-226 (1993).

Copending Application No. I 0/356,641, filed Jun. 20, 2003, Specification and currently pending claims, Current Examiner: Ahmed, Hasan Syed.

Gorman et al., An Evaluation of Croscarmellose as a Tablet Disintegrant in Direct Compression Systems, Drug. Dev. Ind. Pharm. 1982; vol. 8, pp. 397-410.

Handbook (Binran) of Granule, vol. 1, Ohmsha Ltd., p. 434 & 438 (May 3, 1975).

Ishino et al., "Design and Preparation of Pulsatile Release Tablet as a New Oral Drug Delivery System," Chem. Pharm. Bull. 40(11):3036-3041 (1992).

Kaneto et al., 2000, Latest Pharmacy, Hirokawa Publishing Co., 1 Edition, (Extract and English translation thereof).

(56) References Cited

OTHER PUBLICATIONS

Kawashima, "Low-Substituted Hydroxypropylcellulose as a Sustained-Drug Release Matrix Base or Disintegrant Depending on its Particle Size and Loading in Formulation," Pharm. Res. 1993, vol. 10(3), pp. 351-355.
Kornblum, "A New Tablet Disintegrating Agent," J. Pharm. Sci., Jan. 1973, vol. 62(1), pp. 43-49.
Kratochvil et al., "Atomoxetine: a selective noradrenaline reuptake inhibitor for the treatment of attention-deficit/hyperactivity disorder," Expert Opin. Pharmacother. 4(7):1165-1174 (2003).
McKenna et al., "Effect of particle size on the compaction mechanism and tensile strength of tablets," J. Pharm. Pharmacol. Jun. 1982, vol. 34(6), pp. 347-351.
McKETTA et al., "Table of Contents," Encyclopedia of Chemical Processing and Design (1989).
McKETTA et al., Encyclopedia of Chemical Processing and Design, "Organic Phase Separation Conservation," p. 167 (1989).
Mitsuo et al., Pharmaceutics Manual, 1989, Pharmaceutics Manual, Nanzando Co. Ltd. (Extract and English translation thereof).
Nwokole et al., "Tolerance during 29 days of conventional dosing with cimetidine, mizatidine, famotidine or ranitidine," Aliment. Pharmacol. Ther. 4(Suppl. 1):29-45 (1990) Abstract only.
Observations issued by the European Patent Office dated Aug. 16, 2002 regarding European Application No. 0914818 (Applicant Kyowa Hakko Kogyo Co., Ltd.).
Office Action, Mexico patent application No. MX/a/2007/004741, 3 pages, Mexico Patent Office (dated Oct. 12, 2010) with translation.
Oh, "International Preliminary Report on Patentability," 5 pages, from International Appl. No. PCT/US2005/037084, United States Patent and Trademark Office, Alexandria, Virginia, USA (dated Aug. 24, 2007).
Ohira et al., "Effects of Various Histamine $H_2$-Receptor Antagonists on Gastrointestinal Motility and Gastric Emptying," J. Smooth Muscle Res. 29:131-142 (1993) translation.
Opposition Documents related to European Opposition of EP 0914818B1 (Opposition file history as of Mar. 9, 2009, excluding duplicative, purely administrative documents (97 pages total)).
Packard, "Advisory Action Before the Filing of an Appeal Brief," 5 pages from U.S. Appl. No. 11/223,819 (dated Jun. 24, 2010).
Packard, "Office Action Summary," 16 pages from U.S. Appl. No. 11/223,819 (dated Feb. 24, 2009).
Packard, "Office Action Summary," 8 pages from U.S. Appl. No. 11/223,819 (dated Aug. 22, 2008).
Packard, "Office Action Summary," 9 pages from U.S. Appl. No. 11/223,819 (dated Dec. 7, 2009).
Pharmaceutical Excipients. London: Pharmaceutical Press. Electronic Version, 2006, Mannitol.
Pharmaceutical Excipients. London: Pharmaceutical Press. Electronic Version, 2006, Lactose Monohydrate.
Pharmaceutical Excipients. London: Pharmaceutical Press. Electronic Version, 2006, Croscarmellose sodium.
Potenza, Examiner's first report on patent application No. 2005307052, 3 pages, Australia Patent Office (dated Mar. 15, 2010).
Rankin, "International Search Report," 6 pages, PCT International Application No. PCT/US02/39238, European Patent Office (dated May 8, 2003).
Rudnic et al., "Some Effects of Relatively Low Levels of Eight Tablet Disintegrants on a Direct Compression System," Drug. Dev. Ind. Pharm. 1981, vol. 7(3), pp. 347-358.
Rudnic et al., "Studies of the Utility of Cross Linked Polyvinlpolypyrrolidine as a Tablet Disintegrant," Drug Development and Industrial Pharmacy, 1980, vol. 6, No. 3, pp. 291-309.
Sato et al., "Anticonvulsant effects of tigabine, a new antiepileptic drug: the profile of action in the rat kindling model of epilepsy," Epilepsia 37(Supp. 3):110-111 (1996).
Schifferer, "Communication pursuant to Article 94(3) EPC," 3 pages, from European Patent Appl. No. 05851221.1, European Patent Office, Munich, Germany (dated Oct. 13, 2009).
Schifferer, "Communication," 9 pages, from European Pat. Appl. No. 10184903.2, European Patent Office (dated Mar. 17, 2011).
Schifferer, "International Search Report," 4 pages, from International Appl. No. PCT/US2005/037084, European Patent Office, Rijswijk, The Netherlands (dated Jun. 1, 2006).
Schifferer, "Written Opinion of the International Search Authority," 6 pages, from International Appl. No. PCT/US2005/037084, European Patent Office, Munich, Germany (dated Jun. 1, 2006).
Shangraw et al., "A new era of tablet disintegrants," Pharm. Technol. 1980, vol. 4(10), pp. 49-57.
Spear, "Office Action Summary," 16 pages, from U.S. Appl. No. 10/356,641 (dated Dec. 8, 2004).
Tirkkonen and Paronen, "Enhancement of drug release from ethylcellulose microcapsules using solid sodium chloride in the wall," Int. J. Pharmaceutics 88:39-51 (1992).
Trottier and Wood, 2005, "Particle Size Measurement," Kirk-Othmer Encyclopedia of Chemical Technology (Extract of 1. Introduction; 2. Data Representation; 4. Measurement Methods; 8. Selection of Equipment).
Ueki et al., "Nizatidine Comparably Enhances Postprandial Gastric Motility to Existing Gastroprokinetics in Dogs," Jpn. Pharmacol. Ther. 28(11):925-930 (2000) translation.
Uhl, "International Search Report," 5 pages, International Patent Appl. No. PCT/US2006/016538, European Patent Office (dated Feb. 27, 2007).
Uhl, "Written Opinion of the International Searching Authority," 6 pages, International Patent Appl. No. PCT/US2006/016538, European Patent Office (dated Feb. 27, 2007).
Van Kamp et al., "Improvement by super disintegrants of the properties of tablets containing lactose, prepared by wet granulation," Pharmaceutisch Weekblad Scientific Edition; 1983, vol. 5, pp. 165-171.
Villa, "Communication pursuant to Article 94(3) EPC," 3 pages, from European Patent Appl. No. 05818156.1, European Patent Office, Munich, Germany (dated Jul. 1, 2009).
Villa, "Communication pursuant to Article 94(3) EPC," 4 pages, from European Patent Appl. No. 05818156.1, European Patent Office (dated Feb. 25, 2011).
Villa, "European Search Report," 5 pages, from European Patent Appl. No. 11171982.9, European Patent Office, Munich, Germany (dated Dec. 22, 2011).
Villa, "International Search Report," 4 pages, from International Appl. No. PCT/US2005/038328, European Patent Office, Rijswijk, The Netherlands (dated Sep. 15, 2006).
Villa, "Written Opinion of the International Search Authority," 5 pages, from International Appl. No. PCT/US2005/038328, European Patent Office, Munich, Germany (dated Sep. 15, 2006).
Vromans et al., "Studies on tableting properties of lactose," Pharmaceutisch Weekblad Scientific Edition; 1985, vol. 7, pp. 186-193.
Walsh, "Examination Report," 2 pages, from New Zealand Patent Appl. No. 589750, New Zealand Patent Office (dated Dec. 8, 2010).
Walsh, "Examination Report," 2 pages, from New Zealand Patent Appl. No. 554240, New Zealand Patent Office, Wellington, New Zealand (dated Jun. 9, 2009).
Ware, "Office Action Summary," 12 pages, from U.S. Appl. No. 09/147,374 (dated Oct. 14, 1999).
Ware, "Office Action Summary," 6 pages, from U.S. Appl. No. 09/147,374 (dated Jun. 30, 2000).
Ware, "Office Action Summary," 6 pages, from U.S. Appl. No. 09/147,374 (dated Aug. 29, 2001).
Ware, "Office Action Summary," 6 pages, from U.S. Appl. No. 09/147,374 (dated Jun. 4, 2002).
Ware, "Office Action Summary," 8 pages, from U.S. Appl. No. 09/147,374 (dated Apr. 18, 2001).
Welter, "Advisory Action Before the Filing of an Appeal Brief," 4 pages from U.S. Appl. No. 11/248,596 (dated Oct. 13, 2010).
Welter, "Advisory Action Before the Filing of an Appeal Brief," 9 pages from U.S. Appl. No. 11/256,653 (dated Sep. 27, 2010).
Welter, "Office Action Summary," 25 pages from U.S. Appl. No. 11/256,653 (dated Mar. 18, 2010).
Welter, "Office Action Summary," 26 pages from U.S Appl. No. 11/213,266 (dated Nov. 13, 2009).
Welter, "Office Action Summary," 26 pages from U.S. Appl. No. 11/248,596 (dated Mar. 19, 2010).

(56) References Cited

OTHER PUBLICATIONS

Welter, "Office Action Summary," 28 pages from U.S. Appl. No. 11/213,266 (dated Apr. 6, 2009).
Welter, "Office Action Summary," 28 pages from U.S. Appl. No. 11/248,596 (dated Jul. 10, 2008).
Welter, "Office Action Summary," 28 pages from U.S. Appl. No. 11/248,596 (dated Apr. 29, 2009).
Welter, "Office Action Summary," 29 pages from U.S. Appl. No. 11/213,266 (dated Jul. 10, 2008).
Welter, "Office Action Summary," 29 pages from U.S. Appl. No. 11/256,653 (dated Jul. 10, 2008).
Welter, "Office Action Summary," 29 pages from U.S. Appl. No. 11/256,653 (dated May 12, 2009).
Welter, "Office Action Summary," 33 pages from U.S. Appl. No. 11/213,266 (dated Nov. 12, 2010).
Yamahara et al., "Effect of Release Rate on Bioavailability of Control-Release Multiple Unit Dosage Forms," YAKUZAIGAku 55(2):99-107 (1995).
Yamamoto et al., "The Effects of Nizatidine on the Function of Esophageal Motility in Patients with Gastroesophageal Reflux Disease (GERD)," Jpn. Pharmacol. Ther. 28(5):419-424 (2000) translation.
Young, "International Preliminary Examination Report" 6 pages, PCT International Application No. PCT/US02/39238, United States Patent and Trademark Office (dated Apr. 27, 2005).
Young, "International Search Report," 2 pages, PCT appl. No. PCT/US11/20493, United States Patent and Trademark Office (dated Mar. 23, 2011).
Young, "Written Opinion of the International Searching Authority," 6 pages, PCT appl. No. PCT/US11/20493, United States Patent and Trademark Office (dated Mar. 23, 2011).
Young, "Written Opinion," 5 pages, PCT International Application No. PCT/US02/39238, United States Patent and Trademark Office (datedJan. 13, 2005).
Zheng et al., "Influence of Eudragit® NE 30 D Blended with Eudragit® L 30 D-55 on the Release of Phenylpropanolamine Hydrochloride from Coated Pellets," Drug Development and Industrial Pharmacy 29(3):357-366 (2003).
Zimmer, "European Search Report," 3 pages, European patent appl. No. 01103129.1, European Patent Office (dated Jun. 9, 2001).
Zimmer, "International Search Report," 4 pages, PCT International Application No. PCT/US01/04012, European Patent Office (dated Jun. 19, 2001).

TASTE-MASKED PHARMACEUTICAL COMPOSITIONS WITH GASTROSOLUBLE PORE-FORMERS

CROSS REFERENCE TO RELATED APPLICATION

This application is a continuation of U.S. application Ser. No. 11/256,653, filed Oct. 21, 2005, which claims the benefit of U.S. Provisional Application No. 60/621,144, filed Oct. 21, 2004, each of which is herein incorporated by reference in its entirety.

TECHNICAL FIELD

This invention relates to an orally disintegrating tablet (ODT) composition comprising taste-masked microparticles of one or more active pharmaceutical ingredients suitable for oral administration for the treatment of diseases and rapidly-dispersing microgranules comprising a disintegrant and a sugar alcohol or a saccharide, or a mixture thereof, each of which having an average particle diameter of not more than 30 μm. The multi-particulate ODT composition contains rapidly-dispersing microgranules and drug-containing core particles (crystals or granules, beads or pellets of one or more active pharmaceutical ingredients) coated with a taste-masking membrane comprising a water-insoluble polymer in combination with one or more pore-formers such as inorganic or organic salts which are practically insoluble in water and saliva, but soluble in an acidic buffer. The multi-particulate ODT composition rapidly disintegrates on contact with saliva when placed in the oral cavity forming a smooth, easy-to-swallow suspension containing coated panicles exhibiting acceptable taste-masking and provides rapid, substantially-complete release of the dose on entry into the stomach, thereby enhancing the probability of achieving bioequivalence to the reference immediate-release (IR) product. The invention additionally provides a method of manufacturing orally disintegrating tablets comprising rapidly-dispersing microgranules and acceptably taste-masked microparticles (crystals, pellets, granules, or beads containing the drug) with an average particle size of not more than about 400 μm, more particularly not more than about 300 μm, to provide a smooth mouthfeel leaving no aftertaste (non-gritty or non-chalky taste) after swallowing the suspension.

BACKGROUND OF THE INVENTION

There are two types of most widely used dosage forms for medication by oral administration: tablets and capsules. However, such dosage forms have several disadvantages. For example, it is estimated that 50% of the population have problems swallowing tablets (see Seager in Journal of Pharmacol, and Pharm. 50, pages 375-382, 1998); especially it is hard for aged persons to swallow tablets or capsules or to medicate children who are unable or unwilling to swallow tablets or capsules. This leads to poor, even non-compliance with the treatment and thus has a negative impact on the efficacy of the treatment. The bitter taste of many actives precludes the medication from being easily sprinkled onto food such as applesauce, a commonly used method of administering medications to children. The conventional capsule or tablet dosage form is also inconvenient for the 'people on the move' who often do not have access to drinking water or fluids. Chewable tablets comprising taste-masked particles capable of being chewed without experiencing a bitter taste were introduced not too long ago, and these tablets became popular with children.

The bitter drug-containing cores incorporated into chewable tablets have thick coatings of mostly water-insoluble polymers such as ethylcellulose to resist fracture during tablet compression and/or during chewing and concomitant leakage of the bitter active. Consequently, substantially complete release of the drug from such chewable tablets in the gastrointestinal tract takes 2 hours or longer. More recently, orally disintegrating tablet (ODT) dosage forms have been introduced, which rapidly dissolve or disintegrate in the buccal cavity and hence can be taken without water. Such medicines are convenient for all, the aged persons, the children or the 'people on the move'.

An ideal orally disintegrating tablet formulation comprising rapidly-dispersing microgranules and drug-containing microparticles (crystals, pellets, granules, or beads containing the drug) with a taste-masking membrane (if required) should rapidly disintegrate on contact with saliva in the oral cavity forming a smooth, easy-to-swallow suspension containing taste-masked drug particles having an average panicle diameter of not more than about 400 μm to provide a smooth mouthfeel leaving no aftertaste (i.e., little or minimal drug release with a non-gritty or non-chalky taste) until swallowed, and should provide rapid, substantially-complete release upon arrival in the stomach in order to be bioequivalent to the reference product.

As indicated earlier, most of the active pharmaceutical ingredients in the market are bitter to a varying degree. Typically, to eliminate/minimize drug-release in the oral cavity, the bitter drug substance was taste-masked in the prior art by providing a thick polymer-membrane around the drug particle typically by microencapsulation (coacervation by phase separation) or fluid-bed coating for preparing immediate release dosage forms (chewable tablets, sprinkles, sachets, suspensions). However, coating with water-insoluble polymers such as ethylcellulose (EC), cellulose acetate (CA), cellulose acetate phthalate, polyvinyl acetate, Eudragil® RS, RL, L, S and NE30D polymers, results in slower dissolution profiles and not-too-infrequently results in imparting sustained-release properties.

Several marketed products, which are typically conventional or effervescent based immediate-release dosage forms, exhibit a rapid-onset of action with a $T_{max}$ of about an hour or less. An undesirable consequence of taste-masking using a water-insoluble polymer alone or in combination with a water-soluble polymer is in general the slower release of the drug in the gastrointestinal tract, Eudragit E (EPO or E100), a copolymer consisting of dimethylaminoethyl methacrylate and neutral methacrylic acid esters with a weight-average molecular weight of 150,000 and a $pK_a$ of 6.3, is soluble in gastric fluid below pH 5 while it swells and/or is permeable in water and buffer solutions above pH 5.0. The saliva is typically in the pH range of 6.7 to 7.4. Hence, it is likely that one achieves effective taste-masking in the oral cavity, although for very limited time, if the drug core is coated with Eudragit E100/EPO alone or in combination with a water-soluble agent.

From a pharmaceutical and a practical point of view, the inventors of the present invention have examined various methods of taste-masking bitter active pharmaceutical ingredients suitable for incorporation into orally disintegrating tablets having the property of rapidly disintegrating in the buccal cavity and leaving no aftertaste (good creamy mouthfeel) and additionally providing rapid, substantially-complete release of the dose in the stomach, thereby enhancing the probability of achieving bioequivalence to the reference product. The method of producing taste-masked microparticles (mean particle size of about 100-400 μm) in accordance with the present invention comprising one or more bitter active pharmaceutical ingredient(s) includes membrane-coating of drug-containing core panicles (crystals, microgranules, drug-layered or extruded/spheronized-beads) with a mixture of a water-insoluble polymer such as ethylcellulose or polyvinyl acetate and one or more gastrosoluble pore-former(s) such as inorganic or organic salts, at a ratio of about 50/50 to 95/5 for a weight gain of not less than about 5% and not more than about 50% by weight, based on total weight of the coated particle. These gastrosoluble pore-formers are insoluble in both water and saliva, but soluble in a gastric fluid (for example, calcium carbonate or magnesium oxide). Furthermore, the microcapsules prepared in accordance with the present invention can be produced to exhibit the specified criteria (viz., desired panicle size distribution and little or minimal release of the bitter active in the mouth (hence no aftertaste), and rapid-release of the dose from the taste-masked microparticles upon entry into the stomach), to be suitable for incorporation into orally disintegrating tablets.

The taste-masking effectiveness is measured by % of the dose released in a simulated saliva fluid at a pH of 6.7-7.4. The smaller the % release, the more effective the taste-masking. A pharmaceutical composition with not more than 10% of the dose released in about 3 minutes in a simulated saliva fluid (the longest anticipated residence time for taste-masked microparticles in the mouth) is considered acceptably taste-masked. On the other hand, the drug release on oral administration is evaluated by measuring % of the dose released in an acidic pH of about 1.2. The faster the release of the drug from the taste-masked microparticles in the stomach, the higher the probability of being bioequivalent to the reference product. A release of not less than about 60% of the dose in about 30 minutes in the acidic buffer is considered acceptable for achieving bioequivalence to the reference product.

SUMMARY OF THE INVENTION

The present invention provides pharmaceutical compositions and methods for making taste-masked microparticles and orally disintegrating tablets. In accordance with particular embodiments, the compositions provide effective taste-masking, smooth mouthfeel (little or no aftertaste) and rapid/complete release upon reaching the stomach, thereby enhancing the probability of achieving bioequivalence to the reference product.

The multi-particulate compositions comprise taste-masked core particles (crystals or granules, beads or pellets comprising one or more timer-tasting active pharmaceutical ingredients)) with a mixture of a water-insoluble polymer such as ethylcellulose and a gastrosoluble inorganic or organic pore-former such as calcium carbonate. The taste-masking membrane may be applied by fluid bed coating. The taste-masked composition prepared in accordance with the present invention rapidly releases the drug, i.e., not less than about 60% of the dose released in 30 minutes, when tested for dissolution using United States Pharmacopoeia Apparatus 1 (baskets @ 100 rpm) or Apparatus 2 (paddles @ 50 rpm) in 900 mL of 0.1N HCl. Another embodiment of the invention relates to a pharmaceutical composition in the form of an orally disintegrating tablet comprising (i) rapidly-dispersing microgranules containing (a) a disintegrant and (b) a sugar alcohol, a saccharide or combination thereof whose average particle size is not more than about 30 μm, (ii) microparticles of one or more bitter-tasting active pharmaceutical ingredient(s) taste-masked with a polymer membrane comprising a blend of a water-insoluble polymer and a gastrosoluble inorganic or organic pore-former such calcium carbonate, and (iii) optionally other pharmaceutically acceptable excipients. In accordance with particular embodiments, these orally disintegrating tablets have the properties of disintegrating on contact with saliva in the buccal cavity in about 60 seconds forming a smooth easy-to-swallow suspension with no aftertaste (good creamy mouthfeel) and rapidly releasing the dose on entry into the stomach, thus enhancing the probability of being bioequivalent to the reference product.

A taste-masked multiparticulate pharmaceutical composition comprising:
(a) a drug-containing core particle (crystal, granule, pellet, bead and the like);
(b) a taste-masking membrane on said drug-containing core particle comprising a combination of a water-insoluble polymer and a gastrosoluble inorganic or organic pore-former at a ratio ranging from about 95/5 to about 50/50 having a thickness of from about 5% to about 50% based on the weight of the coaled particle and an average panicle size of not more than about 400 μm is disclosed.

The composition typically exhibits acceptable taste-masking when the composition is placed in the oral cavity for 3 minutes, more particularly for 2 minutes, in some cases for 60 seconds, and in particular until it is swallowed leaving little or no aftertaste (i.e., experiencing no gritty or chalky taste) and the composition provides rapid, substantially-complete release of the dose upon entry into the stomach, i.e., releases not less than about 60% of the dose in 30 min when tested for dissolution using United States Pharmacopoeia Apparatus 1 (Baskets@100 rpm in 900 mL of pH 1.2 buffer).

A taste-masked multiparticulate pharmaceutical composition in the ODT (orally disintegrating tablet) form, which disintegrates on contact with saliva in the buccal cavity in about 60 seconds forming a smooth easy-to-swallow suspension (no gritty or chalky aftertaste) is also disclosed. The ODT may comprise the drug-containing core particle (crystal, granule, pellet, bead and the like), with a taste-masking membrane on the drug-containing core particle. The taste-masking membrane may comprise a water-insoluble polymer and 3 gastrosoluble pore-former at a ratio ranging from about 95/5 to about 50/50 having a thickness of from about 5% to about 50% based on the weight of the coated microparticle with an average particle sue of not more than about 400 μm, or in some embodiments not more than about 300 μm. The ODT may also include a rapidly-dispersing microgranule with an average particle size of not more than about 300 μm, or in some embodiments not more than about 200 μm, comprising a disnintegrant and a sugar alcohol, a saccharide or a combination thereof, each having an average particle diameter of not more than about 30 μm, and optionally pharmaceutically acceptable excipients typically used in ODT formulations, viz., flavors, a sweetener, coloring agents, and other disintegrates.

The ODT in accordance with one embodiment exhibits the following properties:
1) disintegrates on contact with saliva m the oral cavity in about 60 seconds forming a smooth, easy-to-swallow suspension comprising taste-masked microparticles, and 2) taste-masked microparticles provide rapid, substantially-complete release of the dose upon entry into the stomach.

The ODT may comprise taste-masked microparticles demonstrating effective taste-masking by releasing not more than 10% in about 3 minutes (the longest typical residence time anticipated for the ODT in the buccal cavity) when dissolution tested in a simulated saliva fluid (pH ~7.0) while releasing not less than 60% of the dose in about 30 minutes when dissolution tested in 0.1 NHCl.

A method of manufacturing a taste-masked multi-particulate composition wherein the dosage form comprises one or more active pharmaceutical ingredient(s) in sufficient quantities to be administered orally to a patient at prescribed dosing regimen to provide therapeutic efficacy is also provided.

The taste-masked multiparticulate pharmaceutical composition may include any pharmaceutically acceptable active ingredient requiring taste-masking.

In accordance with particular embodiments, the method of preparing a taste-masked multi-particulate composition includes layering a pharmaceutically acceptable drug from a polymeric binder solution onto an inert particle selected from the group consisting of sugar spheres and cellulose spheres. Fluid bed or pan coating may be used to apply the active and polymeric binder solution.

In accordance with certain embodiments, the core particles may be crystals with a desired particle size distribution, beads, microgranules or pellets containing one or more active pharmaceutical ingredient(s), requiring taste-masking.

The taste-masked multiparticulate pharmaceutical composition may include a drug-containing core particle that is a drug-layered lead comprising an inert article such as a sugar sphere, a cellulose sphere or a silicon dioxide sphere coated with one or more pharmaceutically acceptable actives from a polymeric binder solution.

In accordance with certain embodiments, the drug-containing particle is a microgranule or an extruded/spheronized pellet comprising one or more pharmaceutically acceptable active ingredient(s), a polymeric binder, which imparts resilient characteristics to dried microgranules, a hydrophilic filler/diluent, and optionally a flavor, a sweetener and/or a disintegrant.

The microgranules of one or more active pharmaceutical ingredient(s) may be prepared by a conventional high-shear or planetary granulation process or the pellets may be prepared by a conventional granulation-extrusion-spheronization process comprising art active pharmaceutical ingredient, a polymer binder and one or more fillers/diluents.

The water-insoluble polymer (e.g., ethylcellulose with an average viscosity of 10 cps) and the gastrosoluble organic or inorganic pore-former (e.g., calcium carbonate or magnesium oxide) may be present at a weight ratio of from about 95/5 to 50/50, more particularly from about 85/15 to 65/35 and the membrane thickness may vary from about 5% to 50%, more particularly from about 10% to 30% by weight in accordance with particular embodiments.

In accordance with some embodiments of the present invention, the taste-masked multiparticulate ODT formulation includes rapidly-dispersing microgranules at about 50% to about 90% by weight of the tablet comprising a disintegrant (e.g., crospovidone), and a sugar alcohol (e.g., mannitol) or a saccharide (e.g., lactose) or a combination thereof, each sugar alcohol or saccharide having an average particle diameter of not more than about 30 µm and a ratio of sugar alcohol or saccharide to disintegrant varying from about 90/10 to about 99/1.

In accordance with particular embodiments of the present invention, the rapidly-dispersing microgranules and taste-masked microparticles may be present in the ratio of about 6/1 to 2/1, more particularly from about 4/1 to 3/1, to achieve a smooth mouth feel.

In accordance with certain embodiments of the present invention, a method of manufacturing a taste-masked multi-particulate composition of one or more active pharmaceutical ingredient(s) is also provided. The method may comprise the steps of:
a) preparing core particles (crystals with a particle size distribution of 20-500 µm, more particularly of 30-300 µm, beads, microgranules or pellets) of one or more active pharmaceutical ingredient(s) as granules by a conventional granulation process, as beads by drug-layering onto inert particles from a polymeric binder solution in fluid-bed equipment, or as microgranules or as pellets by a conventional granulation of one or more active pharmaceutical ingredient(s), one or more polymeric binder(s), a hydrophilic filler/diluent, and optionally a flavor, a sweetener, and/or a disintegrant or granulation-extrusion-spheronization process; and
b) coating core particles by applying a membrane comprising a mixture (at a ratio of 95/5 to 50/50) of water-insoluble ethylcellulose and gastrosoluble inorganic or organic pore-former such as calcium carbonate, dissolved/dispersed in a mixture of acetone and purified water, the membrane coating comprising approximately from about 5% to about 50% based on the total weight of the coated particles.

The composition may exhibit the following properties:
a) acceptable taste-masking when the composition is placed in the oral cavity for 3 minutes, more particularly for 2 minutes and in certain embodiments for 60 seconds, and in still other embodiments, until it is swallowed leaving no aftertaste; and
b) rapid, substantially-complete release of the dose upon entry into the stomach, i.e., releases not less than about 60% of the dose in 30 min when tested for dissolution using United States Pharmacopoeia Apparatus 1 (Baskets@100 rpm) or Apparatus 2 (paddles @ 50 rpm m 900 mL of pH 1.2 buffer).

In accordance with certain embodiments of the present invention, the method comprises the steps of:
a) preparing core particles (crystals with a particle size distribution of 20-500 µm, more particularly of 50-300 µm, beads, microgranules, pellets) of one or more active pharmaceutical ingredients) as described above;
b) taste-masking core particles by applying a membrane comprising a mixture of water-insoluble and gastro-soluble inorganic or organic pore-former as described above, the membrane coating comprising approximately about 5% to 50% based on the total weight of the coated particles;
c) granulating a disintegrant such as Crospovidone with a sugar alcohol or a saccharide, or a combination thereof, each having an average particle diameter of not more than 30 µm, with water or an alcohol-water mixture in a conventional granulator and drying in a fluid bed equipment to produce granules with an average panicle size not more than 400 µm (more particularly not more than 300 µm);
d) blending taste-masked microparticles of step (b) with rapidly disintegrating microgranules of step (c) at a ratio of about 1/6 to about 1/2, and optionally other, pharmaceutically acceptable ingredients, such as a flavoring agent (<0.5% w/w), a coloring agent (<0.5% w/w), a sweetener (<0.5% w/w) and additional disintegrant (up to 5% w/w); and e) compressing into tablets using a conventional rotary tablet press equipped with an external lubrication system to pre-lubricate the dies and punches.

The ODT may exhibit the following properties:
1) disintegrates on contact with the saliva in the oral cavity forming a smooth, easy-to-swallow suspension comprising taste-masked microparticles,
2) leaves no aftertaste after swallowed (no gritty or chalky mouthfeel),
3) provides rapid, substantially-complete release of the dose upon entry into the stomach; or
4) the OUT when tested for dissolution using United States Pharmacopoeia Apparatus 1 (baskets @ 100 rpm) or Apparatus 2 (paddles @ 50 rpm) in 900 ml buffer releases not more than 10% of the dose in about 3 minutes in a simulated saliva buffer at pH 6.8 and not less than about 60% of the dose in about 30 minutes in an acidic buffer at pH 1.2.

These and other embodiments, advantages and features of the present invention become clear when detailed description and examples are provided in subsequent sections.

DETAILED DESCRIPTION OF THE INVENTION

All documents cited are, in relevant part, incorporated herein by reference; the citation of any document is not to be construed as an admission that it is prior an with respect to the present invention.

The term 'drug', 'active' or 'active pharmaceutical ingredient' as used herein is meant to include the base, any pharmaceutically acceptable salt, stereoisomer and mixtures thereof. The term represents any therapeutic agent indicated for oral administration. Examples of therapeutic agents include, but are not limited to, NSAID analgesic, histamine $H_1$-receptor antagonist, histamine, $H_2$-receptor antagonist, 5-$HT_1$ receptor agonist, 5-$HT_3$ receptor antagonist, antiepileptic drug, centrally acting adrenergic agonist, sleep-aid, leukotriene receptor antagonist, and a drug for the treatment of erectile dysfunction requiring taste-masking. Specific examples of the therapeutic agent used in various embodiments of this invention include one or more from the group consisting of sumatriptan, electriptan, cetirizine, zafirlukast, montelukast, famotidine, ranitidine, tiagabine, fexofenadine, tizanidine, alphrazolum, ondansetron, granisetron, zolpidem, zaleplon, sildenafil, tadalafil and the like.

Unless indicated otherwise, all percentages and ratios are calculated by weight.

Unless indicated otherwise, all percentages and ratios are calculated based on the total composition.

An aqueous or a pharmaceutically acceptable solvent medium may be used for preparing drug-containing core particles for taste-masking, viz., beads by drug-layering onto inert sugar spheres in fluid-bed equipment. Examples of useful solvents include, but are not limited to, acetone, ethanol, isopropanol (IPA), water or a mixture thereof. The type of film-forming binder that is used to bind the water-soluble drug to the inert sugar sphere is not critical but usually water-soluble, alcohol-soluble or acetone/water soluble binders are used. A binder such as polyvinylpyrrolidone (PVP), polyethylene oxide, hydroxypropyl methylcellulose (HPMC), hydroxypropylcellulose (HPC), may be used at concentrations of about 0.5 to 10% by weight based on the drug-layered beads. The drug substance may be present in this coating formulation in solution form or may be suspended at a solid content up to 35% by weight depending on the viscosity of the coating formulation.

Crystals of a bitter API with a desired particle size range of from about 20 µm to 500 µm, more particularly from about 50 µm to 300 µm may be taste-masked directly. Alternatively, microgranules containing milted or micronized drug may be produced by granulating in a high-shear granulator the active and a suitable filler/diluent (if required) with a polymeric binder, which imparts resilient characteristics to the dried microgranules to resist attrition due to fluidization during fluid-bed coating for taste-masking. The relative amounts of active, hinder and optional filler/diluent may vary considerably depending on the particular active and the dosage form. Typically, microgranules prepared in accordance with this aspect of the invention will contain from about 5% to about 95%, more particularly from about 20% to about 90%, active and up to about 15% binder with any optional filler/diluent being present at from about 0% to about 90%, more particularly from about 20% to about 80%, by weight of the microgranules.

Examples of useful polymeric binders include, but are not limited to, hydroxypropylcellulose (Klucel® UP from Aqualon), modified starch (e.g., Starch 1551 and Starch 1500, commercially available from National Starch and Colorcon, respectively), Kollidon® VA 64, poly (vinyl acetate-vinyl pyrrolidone) from BASF, and hydroxypropyl methylcellulose with a viscosity of 100 cps or more (e.g., Methocel K100LV and Metolose K400 commercially available from Dow Chemical and Shin Etsu Chemicals, respectively) alone or in combination with a widely used binder such as PVP (polyvinylpyrrolidone) or hydroxypropyl methylcellulose with a viscosity of 15 cps or less.

Examples of useful pharmaceutically acceptable fillers/diluents include, but are not limited to, mannitol, lactose, microcrystalline cellulose, potassium sulfate, calcium phosphate, modified starch and mixtures thereof.

The water-insoluble polymers suitable for taste-masking of bitter drugs by coating in fluid-bed equipment include, but are not limited to, ethylcellulose, cellulose acetate, cellulose acetate butyrate, methacrylate copolymers available under the trade name of 'Eudragit' (type RL, RS and NE30D) and mixtures thereof. The gastrosoluble organic or inorganic pore-former is insoluble in water and saliva but is readily soluble under acidic conditions. Examples of useful pore-formers include, but are not limited to, calcium carbonate, calcium phosphate, calcium saccharide, calcium succinate, calcium tartrate, ferric acetate, ferric hydroxide, ferric phosphate, magnesium carbonate, magnesium citrate, magnesium hydroxide, magnesium phosphate, and the like and mixtures thereof. The ratio of water-insoluble polymer to gastrosoluble organic or inorganic pore-former for producing taste-masked particles may typically vary from about 95/5 to about 50/50, or in some embodiments from about 85/15 to 65/35, at a thickness of from about 5% to about 50%, more particularly from about 10% to about 30%, by weight of the coated bead.

The membranes described herein may also include one or more plasticizers. Representative examples of plasticizers that may be used to plasticize the membranes include triacetin, tributyl citrate, triethyl citrate, acetyl tri-n-butyl citrate, diethyl phthalate, castor oil, dibutyl sebacate, acetylated monoglycerides and the like or mixtures thereof. The plasticizer may comprise typically about 10-30% or about 5-15% based on the weight of dry polymer, depending on the use of polymer dispersions or solutions.

The ODT compositions described herein also include rapidly-dispersing microgranules. One or more sugar alcohols and/or saccharides and a disintegrant are granulated in a high shear granulator and dried in a fluid bed equipment to produce rapidly-dispersing microgranules. Rapidly dispersing microgranules typically will contain disintegrant and sugar alcohol and/or saccharide at a ratio varying from about 90/10 to about 99/1, or in some embodiments from about 90/10 to about 95/5 by weight. Examples of useful sugar alcohols include, without limitation, mannitol, sorbitol, xylitol, maltitol and mixtures thereof. Examples of useful saccharides include, but are not limited to, lactose, sucrose, maltose and mixtures thereof. Each sugar alcohol or saccharide is characterized by an average particle size of not more than about 30 μm. A disintegrant or a so-called super-disintegrant may be selected from the group consisting of crospovidone (crosslinked PVP), sodium starch glycolate, crosslinked sodium carboxymethyl cellulose, low substituted hydroxypropylcellulose and mixtures thereof.

The ODT compositions may also include additional disintegrant separate from the rapidly dispersing microgranules. The additional disintegrant may be present in the ODT formulation at up to about 10% based on the tablet weight.

It is to be understood that while the invention has been described in conjunction with specific embodiments thereof, that the description above as well as the examples that follow are intended to illustrate and not limit the scope of the invention. Any modification within the scope of the invention will be apparent to those skilled in the art to which the invention pertains.

An exemplary method of producing taste-masked microparticles (mean particle size of about 100-400 μm) comprising one or more bitter active pharmaceutical ingredient(s) includes (i) preparing drug-containing particles (crystals with a desired particle size range, microgranules, drug-layered or extruded/spheronized-beads) and (ii) membrane-coating the drug-containing panicles for taste-masking. Crystals of a bitter API may be directly taste-masked if the drug substance with a desired particle size range of from about 20 μm to 500 μm, more particularly from about 50 μm to 300 μm, is available. Drug-containing particles for taste-masking may be produced by the other methods as well in accordance with other aspects of the invention. The method of producing drug-layered beads in one embodiment of the invention comprises dissolving or suspending one or more active pharmaceutical ingredients in a polymeric binder solution and layering onto inert particles such as sugar spheres or Celphere (50-100 mesh or 150-300 μm) using a fluid-bed coater equipped with a bottom-spray Wurster insert. Alternatively, another embodiment for producing resilient drug-containing microgranules, which undergo little or minimal attrition during membrane coating in fluid-bed equipment, includes granulating one or more actives and a filler or diluent (if needed) with a polymeric binder solution in a high-shear granulator. Yet another embodiment of the method of producing drug-containing beads involves granulating the active in a high-shear granulator as described above, followed by extrusion and spheronization of the wet mass using extrusion-spheronization equipment.

The method of producing taste-masked microparticles (crystals, microgranules, drug-layered or extruded/spheronized-beads) in accordance with one aspect of the invention includes fluid-bed coating with a mixture of a water-insoluble polymer such as ethylcellulose or polyvinyl acetate and a gastrosoluble inorganic or organic pore-former such as calcium carbonate or magnesium oxide at a ratio of about 50/50 to 95/05, more particularly from about 85/15 to 65/35, for a weight gain of from about 5% to about 50%, more particularly from about 10% to about 30%.

One specific embodiment of the invention comprises dissolving water-insoluble ethylcellulose in a 95/5 acetone/water with triethyl citrate (TEC) as the plasticizer (at about 10% of the weight of ethylcellulose) and suspending micronized calcium carbonate and coating the drug-cores (crystals, drug-layered beads, microgranules or pellets) in a fluid-bed coater equipped with a bottom-spray Wurster insert.

The invention also provides a method of manufacturing orally disintegrating tablets, produced by mixing the taste-masked microparticles, rapidly-dispersing microgranules and optionally other excipients (for example: flavor, color, sweetener, additional disintegrant, etc.) to form a blend and compressing the blend into orally disintegrating tablets. In accordance with certain aspects of the invention, the orally disintegrating tablets rapidly disintegrate on contact with saliva in the buccal cavity leaving little or no aftertaste (good creamy mouth feel) and provide rapid, substantially-complete release of the dose in the stomach, thereby enhancing the probability of achieving bioequivalence to the reference product.

Rapidly-dispersing microgranules may be produced in accordance with the method of manufacturing rapidly-dispersing microgranules disclosed in co-pending and commonly assigned U.S. patent application Ser. No. 10/827,106, filed Apr. 19, 2004 and co-pending U.S. patent application Ser. No. 11/213,266 filed Aug. 26, 2005. Rapidly dispersing microgranules with an average panicle size of about 125-300 μm, more particularly from about 150-200 μm, comprising a disintegrant (for example, Crospovidone XL-10) and a sugar alcohol or a saccharide or a mixture thereof (for example, D-mannitol) having an average particle diameter of not more than about 30 μm, may be produced by granulating with only water in a high-shear granulator, wet milling and drying in fluid bed equipment. The taste-masked microparticles produced in accordance with the present invention and rapidly-dispersible microgranules may be blended with other pharmaceutically acceptable ingredients and compressed into tablets, which rapidly disintegrate (e.g., typically in less than about 60 seconds) in the buccal cavity with a smooth creamy mouth feel.

In yet another embodiment of the invention, a method to manufacture orally disintegrating tablets is provided. The orally disintegrating tablets may be formed by compressing in a tablet press equipped with an externally lubricating system to pre-lubricate dies and punches and the tablet formulation otherwise being free of lubricant. The orally disintegrating tablets thus produced typically exhibit sufficient hardness and sufficiently low friability and are suitable for packaging in HDPE bottles and push-through blister packs using conventional equipment for storage, transportation and commercial distribution.

The pharmaceutical taste-masked multi-particulate composition in accordance with certain embodiments provides acceptable taste-masking when placed in the mouth until swallowed (target specification: not more than about 10% of the dose released in about 3 minutes when tested for dissolution in simulating saliva fluid at pH about 7.0). If the composition is in the ODT (orally disintegrating tablet) form, the tablet typically will disintegrate on contact with saliva in the buccal cavity in about 60 seconds forming a smooth, easy-to swallow suspension, comprising taste-masked microparticles with acceptable aftertaste. These taste-masked microparticles typically provide substantially-complete release of the dose on entry into the stomach (target specification: not less than about 60%, more particularly not less than about 75% and in accordance with certain embodiments not less than about 80% of the dose released in about 30 minutes when tested for dissolution in simulated gastric fluid or 0.1 N HCl at pH 1.2).

In accordance with one aspect of the invention, a method of manufacturing taste-masked microparticle composition of one or more bitter-tasting therapeutic agents(s), which exhibits acceptable taste-masking when placed in the oral cavity and provides rapid-release of the dose on entry into the stomach, comprises the following steps:
  (a) preparing a drug-containing core particle (crystal with a particle size distribution of 20-500 µm, bead, pellet or granule) by (i) drug-layering on an inert particle (e.g., 50-100 mesh sugar sphere or cellulose sphere (e.g., Celphere® CP-203 available from Asahi Kasei Chemicals Corporation)) from a solution/suspension comprising a polymeric binder and the drug in a fluid-bed coater and coating with a seal-coat (e.g., Opadry® Clear), or (ii) granulating the drug and a filler/diluent such as lactose, mannitol or microcrystalline cellulose with a polymeric binder in a high-shear granulator, or (iii) granulating as above, followed by extrusion and spheronization; and
  (b) coating the core particles with a solution/suspension of a water-insoluble functional polymer and a gastro-soluble organic or inorganic pore-former (for example, ethylcellulose/calcium carbonate at a ratio ranging from about 50/50 to 95/5, more particularly from about 60/40 to 90/10 and in certain embodiments from about 65/35 to 85/15, for a weight gain of about 5% to 50%, more particularly from about 10% to 45% and in certain embodiments from about 15% to 30%) to produce effectively taste-masked microparticles with a desired particle size distribution (an average particle size of not more than about 400 µm, more particularly not more than about 300 µm).

In accordance with another aspect of the invention, the method of manufacturing orally disintegrating tablets, which disintegrate on contact with saliva in the buccal cavity forming a smooth, easy-to swallow suspension with acceptable aftertaste, comprising taste-masked microparticles, which rapidly release the dose on entry into the stomach, comprises the following steps:
  (a) preparing a drug-containing core particle (crystal with a particle size distribution of 20-500 µm, bead pellet or granule) by (i) drug-layering on an inert particle (e.g., 50-100 mesh sugar sphere or cellulose sphere, e.g., Celphere® CP-203) from a solution/suspension comprising a polymeric binder and the drug in a fluid-bed coater and applying a seal-coat (e.g., Opadry® Clear), or (ii) granulating the drug and a diluent/filler such as lactose, mannitol or microcrystalline cellulose with a polymeric binder in a high-shear granulator, or (iii) granulating as above, followed by extrusion and spheronization;
  (b) coating core particles with a solution/suspension of a water-insoluble functional polymer and a gastrosoluble organic or inorganic pore-former (e.g., ethylcellulose/calcium carbonate at a ratio ranging from about 50/50 to 95/5) to produce effectively taste-masked microparticles with a desired particle size distribution (an average particle size of not more than about 400 µm, more particularly not more than about 300 µm);
  (c) granulating a sugar alcohol or a saccharide, or a combination thereof, each of which has an average particle diameter of not more than about 30 µm, with a disintegrant such as Crospovidone using water or an alcohol-water mixture in a typical granulator and drying in fluid-bed equipment to produce rapidly-dispersing microgranules with an average particle size of not more than about 400 µm (typically the average particle size will be in the range of about 100-300 µm);
  (d) blending taste-masked microparticles of step (b) with rapidly-dispersing microgranules of step (c) at a ratio of from about 1/6 to 1/2, more particularly from about 1/4 to 1/3, and optionally other acceptable ingredients such as a flavoring agent, a coloring agent, and a sweetener in sufficient quantities typically up to about 1%, more particularly about 0.5% and additional disintegrant up to about 5%, more particularly about 4% based on the tablet weight; and
  (e) compressing into tablets using a conventional rotary tablet press equipped with an external lubrication system to pre-lubricate the dies and punches.

In Vitro Dissolution Testing:

The taste-masking property of the taste-masked microparticles and the orally disintegrating tablets may be evaluated in the mouth by determining the percentage of drug-release (a release of not more than about 10% of the dose in about 3 minutes is considered acceptable) when tested for dissolution using USP Apparatus 1 (baskets @ 100 rpm) or 2 (paddles @ 50 rpm) in 900 mL of saliva-simulating fluid (at a pH of about 7.0). Further, the rapid-release property in the stomach of the taste-masked microparticles and the orally disintegrating tablets may be evaluated by determining the percentage of drug-release (a release of not less than about 60% of the dose in about 30 minutes is considered acceptable) when tested for dissolution using USP Apparatus 1 (baskets @ 100 rpm) or Apparatus 2 (paddles @ 50 rpm) in 900 mL of 0.1N HCl (at pH 1.2).

In accordance with certain embodiments of the invention, the taste-masked pharmaceutical composition is in the form of a tablet and exhibits low friability in order to be suitable for packaging blisters and bottles for storage, transportation and commercial distribution. Friability can be determined in accordance with the standard pharmaceutical test methods mat are well known to those skilled in the art. Friability for tablets produced in accordance with certain aspects of the invention will have a friability of not more than about 1% and in accordance with certain embodiments not more than about 0.5%.

The following non-limiting examples illustrate the taste-masked microparticle composition or an orally disintegrating tablet dosage form comprising one or more thereapeutic agent(s) requiring taste-masking, manufactured in accordance with the invention, which exhibits acceptable taste-masking when placed in the mouth and substantially complete, rapid-release of the dose on entry into the stomach. All percentages and ratios are by weight unless indicated otherwise.

Example 1

Drug-Layered Diphenhydramine Hydrochloride Beads (Drug Load: 15%):

Diphenhydramine hydrochloride (375 g) was slowly added to an aqueous solution of 41.8 g polyvinylpyrrolidone (binder) and 1667 g of purified water and mixed well. 60-80 mesh sugar spheres (1470 g) were coated with the drug-layering formulation in a Glatt GPCG 3. The drug containing pellets were dried, and a seal coat of Opadry Clear for a weight gain of 4% was applied on the drug-layered beads.

Figure 1:
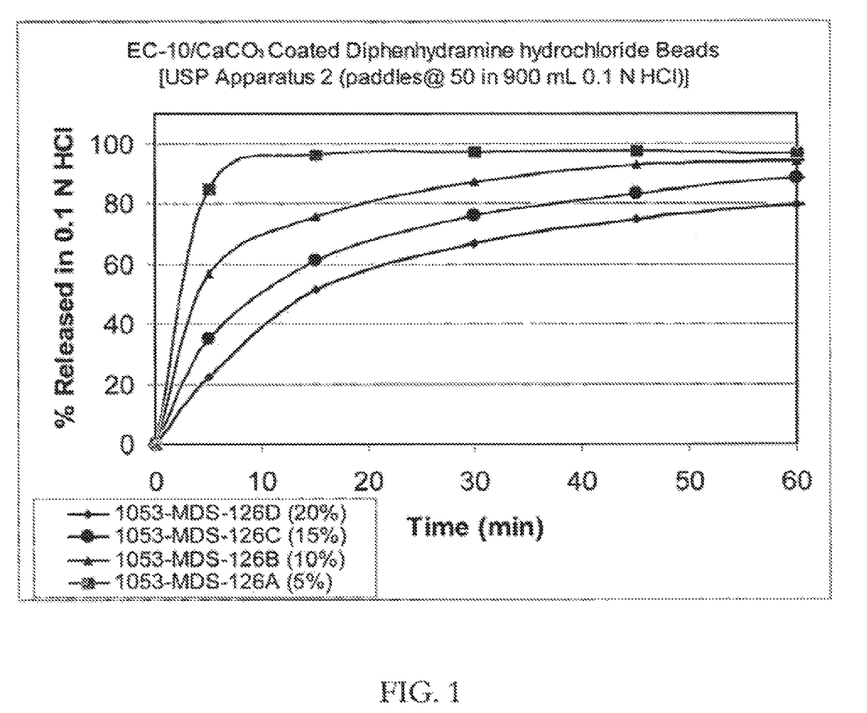
FIG. 1 illustrates the impact of the pore-former on the dissolution in 0.1N HCl of taste-masked diphenhydramine hydrochloride beads of Example 1.

Taste-Masked Beads with Ethylcellulose (EC-10)/Calcium Carbonate:

1000 g of drug-layered beads produced above were coated in the Glatt GPCG 3 with a membrane comprising 227.3 g of EC-10, 22.7 g of Myvacet 9-45 (diacetylated monoglycerine) and 68.2 g of calcium carbonate dissolved/suspended in 3916.6 g of 95/5 acetone/water. The coated beads were dried in the Glatt GPCG-3. The dissolution profiles in 0.1 N HCl of the beads with a membrane thickness of up to 20% by weight are shown in FIG. 1.

Example 2 (Reference): Taste-Masked Beads with Ethylcellulose (EC-10) Alone

Figure 2:
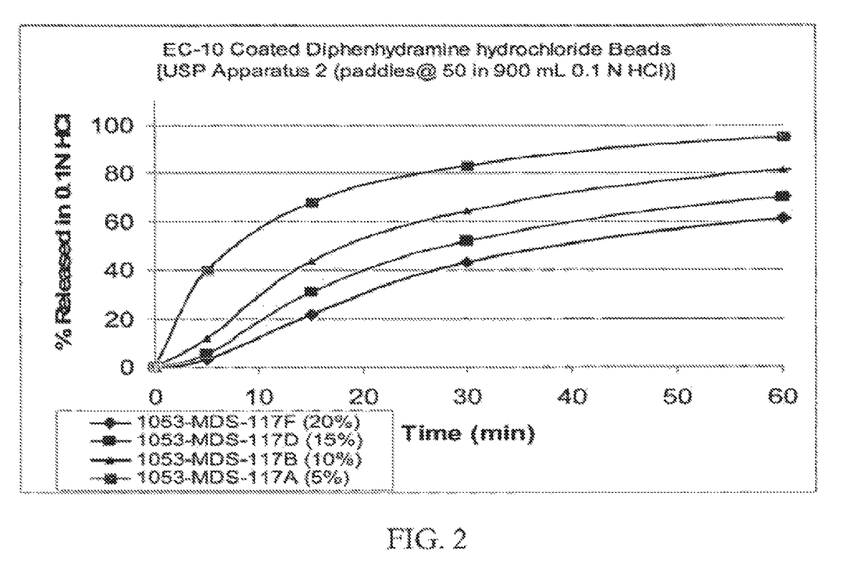
FIG. 2 illustrates the dissolution profiles in 0.1N HCl of diphenhydramine chloride beads taste-masked with Ethylcellulose alone of Example 2.

IR beads were coated with a solution of EC-10/Myvacet 9-45 at a ratio of 90/10 dissolved in 95/5 acetone/water for a weight gain of up to 20%. The coated beads were dried in the Glatt GPCG-3. The taste-masked beads coated at 20% typically release less than about 10% in 5 minutes when dissolution tested using the USP Apparatus 2 (paddles @ 50 rpm) in a phosphate buffer at pH 6.8. The dissolution profiles in 0.1 N HCl of the beads with a membrane thickness of up to 20% by weight are shown in FIG. 2 suggesting that both taste-masking and rapid release can be achieved when coated with ethylcellulose alone from a solvent mixture although the dissolution profiles from the beads thus coated at acceptable taste-masking levels do not meet the desired dissolution profile for a corresponding immediate release product.

Rapidly Dispersing Microgranules:

The rapidly dispersing microgranules may comprise a sugar alcohol such as mannitol and/or a saccharide such as lactose and a disintegrant such as crosslinked povidone (Crospovidone). Typically, mannitol and crospovidone with an average particle size of less than 30 μm are granulated at a ratio of about 95/5 m a high shear granulator such as GMX 600 and dried in a fluid-bed drier such as Glatt GPCG 200 to produce rapidly dispersing microgranules.

OPT Diphenhydramine Hydrochloride:

208 pans of taste-masked beads at 20% coating and 624 parts of the mix (93.38%, rapidly-dispersing microgranules. 5.91% crospovidone, 0.35% orange flavor, and 0.35% Aspartame) would be blended together and compressed into 832 mg tablets containing 25 mg of diphenhydramine hydrochloride with an average hardness of >5 kP. The tablets would release not mote than about 10% in about 5 minutes when dissolution tested using the USP Apparatus 2 (paddles @ 50 rpm) at pH 6.8. In contrast, not less than about 75% of the active would be released in about 45 minutes when dissolution tested in 900 mL 0.1N HCl using USP Apparatus 2 (paddles @ 50 rpm).

Example 3

Figure 3:
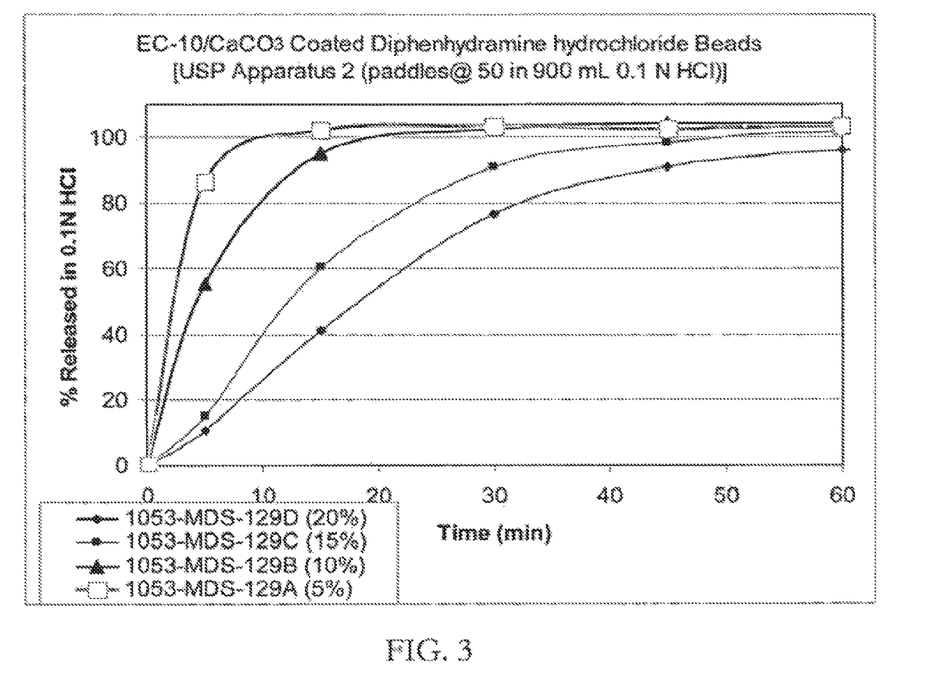
FIG. 3 illustrates the impact of the pore former on the dissolution profiles in 0.1N HCl of taste-masked diphenhydramine hydrochloride beads of Example 3.

Taste-Masked Beads with Polyvinyl Acetate/Calcium Carbonate:

1000 g of drug-layered beads were coated in the Glatt GPCG 3 with a membrane comprising 550 g of Kollicoat SR30D (30% polyvinyl acetate aqueous dispersion), 5.8 g of Myvacet, 495 g of micronized calcium carbonate and 30 g of magnesium stearate dissolved/suspended in 2760.9 g of ethanol (final ratio of ethanol/water: 87/13). The coated beads were dried in the Glatt GPCG-3. The dissolution profiles in 0.1N HCl of the beads with a membrane thickness of up to 20% by weight are shown in FIG. 3.

Example 4 (Reference): Taste-Masked Beads with Polyvinyl Acetate Alone

Figure 4:
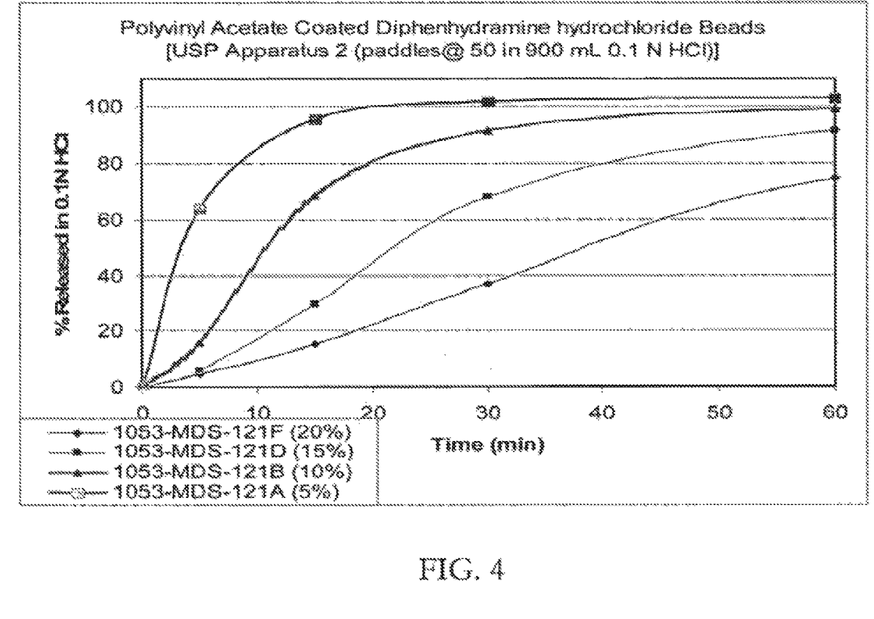
FIG. 4 illustrates the dissolution profiles in 0.1N HCl of diphenhydramine hydrochloride beads taste-masked with polyvinyl acetate alone of Example 4.

IR beads produced in Example 1 were coated with a solution/suspension of polyvinyl acetate (Kolloidon SR30D) with Myvacet 9-45/talc at 2.9/11.5 dissolved in 87/13 ethanol/water for a weight gain of up to 20%, The coated beads were dried in the Glatt GPCG-3. The taste-masked beads coated at 20% typically release leas than about 10% in 5 minutes when dissolution tested using the USP Apparatus 2 (paddles @ 50 rpm) in a phosphate buffer at pH 6.8. The dissolution profiles in 0.1K HCl of die beads with a membrane thickness of up to 20% by weight are shown in FIG. 4.

Based on these observations as well as the observations in Example 1, it is amply clear that both effective taste-masking and rapid dissolution in acidic buffers can be achieved when active-containing cores are coated with a water-insoluble polymer (e.g., ethylcellulose or polyvinyl acetate) alone from a solvent mixture although the dissolution profiles from the beads thus coated at acceptable taste-masking levels may not provide the dissolution profiles corresponding to an immediate release formulation.

Example 5

Drug-Layered Cetirizine Dihydrochloride Beads (Drug Load: 8.4%):

Cetirizine dihydrochloride (180 g) was slowly added to an aqueous solution of 15.7 g polyvinylpyrrolidone (binder) and 782.8 g of purified water and mixed well. 60-80 mesh sugar spheres (1900 g) were coaled with the drug-layering formulation in a Glatt GPCG 3. The drug containing pellets were dried, and a seal coal of Opadry Clear for a weight gain of 2% was applied on the drug-layered beads.

Figure 5:
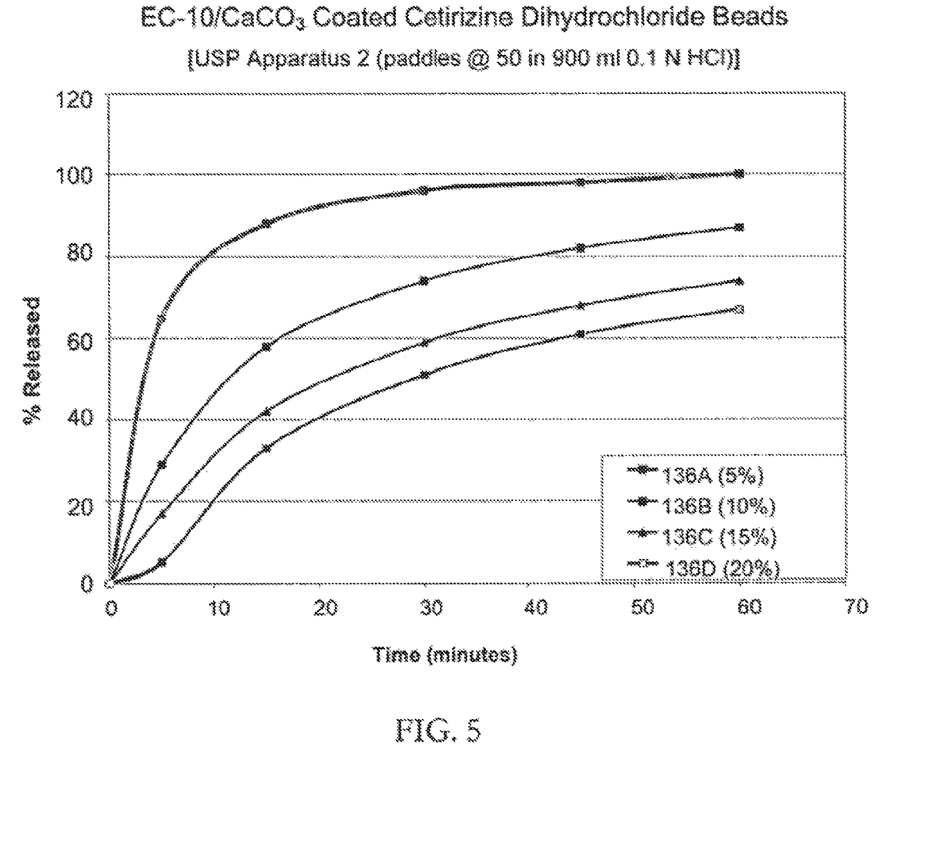
FIG. 5 illustrates the dissolution profiles in 0.1N HCl of Cetirizine dihydrochloride beads taste-masked with Ethylcellulose/calcium carbonate of Example 5.

Taste-Masked Beads with Ethylcellulose/Calcium Carbonate:

IR beads produced above were coated with a solution/suspension of EC-10/Myvacet 9-45/calcium carbonate at a ratio of 71.5/7.1/21.4 in 2620.8 g of 95/5 acetone/water for a weight gain of up to 20%. The coated beads were dried in the Glatt GPCG-3. The taste-masked beads coated at 20% released 13% in 5 minutes when dissolution tested using the USP Apparatus 2 (paddles @ 50 rpm) in a phosphate butter at pH 6.8. The dissolution profiles in 0.1 N HCl of the beads with a membrane thickness of up to 20% by weight are shown in FIG. 5.

ODT Cetirizine Dihydrochloride:

744 g of taste-masked beads at 20% coating, 1734 g of rapidly-dispersing microgranules, 110 g of crospovidone, 13 g orange flavor, and 13 g of Aspartame) would be blended together and compressed into 520 mg tablets containing 10 mg of cetirizine dihydrochloride with an average hardness of >5 kP. The tablets would release not more than 10% in about 5 minutes when dissolution tested using the USP Apparatus 2 (paddles @ 50 rpm) at pH 6.8. In contrast, not less than 75% of the active would be released in about 45 minutes when dissolution tested in 900 mL 0.1N HCl using USP Apparatus 2 (paddles @ 50 rpm).

Example 6

Taste-Masked Microparticles of Sumatriptan Succinate (Drug Load: Approximately 63% of Sumatriptan Succinate):

Sumatriptan succinate (90%) was granulated with an aqueous solution (25% solids) of hydroxypropyl methylcellulose (Methocel K100LV at 10% by weight of the drug) in a high-shear granulator and tray-dried in a convection oven. The resilient granules with an average particle size of about 200 μm would be coated with a 95/5 acetone/water solution/suspension (10% solids) containing 68/7/25 Ethocel (EC-10)/TEC/calcium carbonate m a fluid-bed coater for a weight gain of up to 30%. The coated granules coated 30% would release less than about 10% active in 5 minutes at pH 6.8. Yet the taste-masked beads would release not less than about 75% in 45 minutes when dissolution tested in 0.1N HCl.

Sumatriptan Succinate OPT, 100 mg (as Sumatriptan):

2,160 g of taste-masked microparticles and 3,720 g of rapidly-dispersing microgranules would be blended with crospovidone (72 g), a strawberry flavor (18 g), Aspartame (30 g) and compressed into tablets with an average weight of 1,500 mg and average hardness of >7 kP to demonstrate robustness of the manufacturing (taste-masking and tableting) process and meeting drug-release specifications when dissolution tested in simulated saliva and 0.1 N HCl.

Changes may be made by persons skilled in the art in the composition and the manufacturing procedures as described herein or in the steps or the sequence of steps of the method of manufacture described therein without departing from the spirit and scope of the invention as described above.

What is claimed is:

1. A pharmaceutical composition comprising:
   (1) a plurality of taste-masked particles, wherein each taste-masked particle comprises:
   (a) a drug-containing core particle;
   (b) a taste-masking membrane disposed on said drug-containing core particle comprising a combination of (i) a water-insoluble polymer and (ii) a gastrosoluble inorganic or organic pore-former at a ratio ranging from about 85/15 to about 65/35, wherein the water-insoluble polymer is selected from the group consisting of ethyl cellulose, polyvinyl acetate, cellulose acetate, cellulose acetate phthalate, cellulose acetate butyrate, methacrylate copolymers and combinations thereof, and the gastrosoluble organic or inorganic pore-former is selected from the group consisting of calcium carbonate, calcium phosphate, calcium saccharide, calcium succinate, calcium tartrate, ferric acetate, ferric hydroxide, ferric phosphate, magnesium carbonate, magnesium citrate, magnesium hydroxide, magnesium oxide, magnesium phosphate and mixtures thereof, and the composition releases greater than or equal to about 60% of the total amount of drug in 30 minutes when tested for dissolution using United States Pharmacopoeia Apparatus 2 using paddles at 50 rpm in 900 mL of pH 1.2 buffer; and
   (2) a plurality of rapidly-dispersing microgranules having an average particle size of not more than about 400 μm comprising (i) a disintegrant and (ii) a sugar alcohol or a saccharide or a combination thereof, wherein each of said disintegrant and sugar alcohol or saccharide is present in the form of particles having an average particle diameter of not more than about 30 μm, wherein the ratio of said sugar alcohol, said saccharide or combination thereof to said disintegrant in the rapidly-dispersing microgranules is from about 90/10 to about 99/1; wherein the pharmaceutical composition is an orally disintegrating tablet.

2. The pharmaceutical composition of claim 1, wherein said taste-masked particles release less than or equal to about 10% of the total amount of drug in about 3 minutes when dissolution tested in simulated saliva fluid at about pH 6.8.

3. The pharmaceutical composition of claim 1, comprising one or more drug(s) present in a therapeutically effective amount.

4. The pharmaceutical composition of claim 1, wherein the drug is selected from the group consisting of diphenhydramine, ranitidine, famotidine, cetirizine, fexofenadine, sumatriptan, eletriptan, zolmitriptan, ondansetron, granisetron, tiagabine, tizanidine, zolpidem, zaleplon, zafirlukast, montelukast, sildenafil, tadalafil, pharmaceutically acceptable salts thereof, and combinations thereof.

5. The pharmaceutical composition of claim 1, wherein the drug-containing particle comprises a drug-layered bead comprising an inert particle coated with one or more pharmaceutically acceptable drug(s).

6. The pharmaceutical composition of claim 1, wherein the drug-containing particle comprises a microgranule or an extruded and/or spheronized pellet comprising: 1) one or more pharmaceutically acceptable drug(s), 2) a polymeric binder, and 3) a filler and/or diluent.

7. The pharmaceutical composition of claim 1, wherein said drug requires taste-masking.

8. The pharmaceutical composition of claim 1, wherein the membrane thickness ranges from about 5% to 50% by weight of the coated particle.

9. The pharmaceutical composition of claim 1, wherein the water-insoluble polymer comprises ethylcellulose and the gastrosoluble pore former comprises calcium carbonate.

10. The pharmaceutical composition of claim 1, wherein the ratio of rapidly-dispersing microgranules to taste-masked particles ranges from about 6/1 to about 2/1.

11. The pharmaceutical composition of claim 1, wherein the rapidly-dispersing microgranules comprise a disintegrant selected from the group consisting of crosslinked polyvinylpyrrolidone, sodium starch glycolate, crosslinked sodium carboxymethylcellulose, low-substituted hydroxypropylcellulose and mixtures thereof.

12. The pharmaceutical composition of claim 1, wherein the average particle size of the drug-containing core particle is less than or equal to about 400 μm.

13. The pharmaceutical composition of claim 1, wherein said orally disintegrating tablet has a friability of less than or equal to about 1%.

14. The pharmaceutical composition of claim 1, wherein said orally disintegrating tablet disintegrates on contact with saliva in an oral cavity within approximately 60 seconds.

15. The pharmaceutical composition of claim 1, wherein the rapidly dispersing microgranules comprise a sugar alcohol or a saccharide selected from the group consisting of mannitol, xylitol, sorbitol, maltol, maltitol, lactose, sucrose, maltose, and combinations thereof.

16. The pharmaceutical composition of claim 1, wherein the gastrosoluble organic or inorganic pore former is a salt.

17. The pharmaceutical composition of claim 1, wherein the pharmaceutical composition exhibits acceptable taste-masking when placed in the oral cavity for 60 seconds.

18. The pharmaceutical composition of claim 1, wherein the rapidly dispersing microgranules have an average particle size of less than or equal to about 300 µm.

19. A method of manufacturing a pharmaceutical composition comprising:
(a) preparing core particles comprising a drug;
(b) coating the core particles by applying a membrane comprising a mixture of (i) water-insoluble polymer and (ii) a gastrosoluble organic or inorganic pore former present at a ratio of from about 85/15 to about 65/35 wherein the water-insoluble polymer is selected from the group consisting of ethyl cellulose, polyvinyl acetate, cellulose acetate, cellulose acetate phthalate, cellulose acetate butyrate, methacrylate copolymers and combinations thereof, and the gastrosoluble organic or inorganic pore-former is selected from the group consisting of calcium carbonate, calcium phosphate, calcium saccharide, calcium succinate, calcium tartrate, ferric acetate, ferric hydroxide, ferric phosphate, magnesium carbonate, magnesium citrate, magnesium hydroxide, magnesium oxide, magnesium phosphate and mixtures thereof;
(c) granulating particles of a sugar alcohol or a saccharide, or a combination thereof, each particle of sugar alcohol or saccharide having an average particle diameter of not more than 30 µm, with a disintegrant having an average particle diameter of not more than 30 µm to produce rapidly-dispersing microgranules with an average particle size of not more than about 400 µm, wherein the ratio of said sugar alcohol, said saccharide or combination thereof to said disintegrant in the rapidly-dispersing microgranules is from about 90/10 to about 99/1;
(d) blending the membrane coated particles of step (b) with the rapidly-dispersing microgranules of step (c) at a ratio of about 1/6 to about 1/2; and
(e) compressing the blend of step (d) into orally disintegrating tablets.

20. The method of claim 19, wherein the water-insoluble polymer comprises ethyl cellulose and the gastrosoluble organic or inorganic pore former comprises calcium carbonate.

21. The method of claim 19, wherein said step of compressing (e) comprises utilizing a conventional rotary tablet press equipped with an external lubrication system to pre-lubricate the dies and punches.

22. The method of claim 19, wherein the orally disintegrating tablets, when tested for dissolution using United States Pharmacopoeia Apparatus 2 using paddles at 50 rpm in 900 mL buffer, release less than or equal to about 10% of the total amount of the drug in about 3 minutes in a simulated saliva buffer at pH 6.8 and greater than or equal to about 60% of the total amount of the drug in about 30 minutes in an acidic buffer at pH 1.2.

23. The method of claim 19, wherein said rapidly-dispersing microgranules have an average particle size of not more than 300 µm.

24. The method of claim 19, wherein the membrane is present in an amount of from about 5% to about 50% based on the total weight of the coated particles.

25. The method of claim 19, wherein the pharmaceutical composition exhibits acceptable taste-masking when the composition is placed in the oral cavity for 60 seconds.

26. The method of claim 19, wherein the pharmaceutical composition releases greater than or equal to about 60% of the total amount of the drug in 30 minutes when tested for dissolution using United States Pharmacopeia Apparatus 2 using paddles at 50 rpm in 900 mL of pH 1.2 buffer.

* * * * *